United States Patent
Koini et al.

(10) Patent No.: US 6,350,440 B1
(45) Date of Patent: Feb. 26, 2002

(54) MIXTURES OF VOLATILE LINEAR SILOXANES

(75) Inventors: Thomas Koini, Burghausen; Thomas Köhler, Kastl; Annemarie Huber, Haiming; Manfred Meisenberger, Burghausen, all of (DE); Marianne D. Berthiaume, Tecumseh, MI (US)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/374,179

(22) Filed: Aug. 13, 1999

(30) Foreign Application Priority Data

Aug. 20, 1998 (DE) .......................................... 198 37 850

(51) Int. Cl.$^7$ ............................ A61K 7/48; A61K 7/06; C08G 77/04; C08L 83/04
(52) U.S. Cl. ...................... 424/70.12; 424/401; 424/59; 424/61; 424/63; 424/64; 424/65; 424/70.12; 424/76.1
(58) Field of Search ............................ 424/401, 59, 61, 424/63, 64, 65, 70.1, 70.12, 76.1

(56) References Cited

U.S. PATENT DOCUMENTS

| 4,331,167 A | 5/1982 | Wajaroff ........................ 132/7 |
| 5,002,762 A | 3/1991 | Bolich, Jr. ................... 424/70 |
| 5,084,577 A | 1/1992 | Bolich, Jr. .................. 548/110 |

FOREIGN PATENT DOCUMENTS

| DE | 33 19 764 A1 | 12/1983 |
| EP | 0 400 546 A1 | 5/1990 |
| EP | 0 515 082 A1 | 5/1992 |
| EP | 0 774 482 A2 | 11/1996 |
| FR | 2 771 003 A1 | 5/1999 |
| WO | 98 324 18 A1 | 7/1998 |

OTHER PUBLICATIONS

Derwent Abstract Corresponding to DE 3319764 A (AN 1984–001030) 1984.
Derwent Abstract Corresponding to FR 2771003 A (AN 1999–277177) 1999.

Primary Examiner—Richard L. Raymond
(74) Attorney, Agent, or Firm—Brooks & Kushman P.C.

(57) ABSTRACT

The invention relates to mixtures of linear organosiloxanes of the general formula 1

$$R_3SiO-(SiR_2O)_n-SiR_3 \qquad (1),$$

where

R can be identical or different and is a hydrocarbon radical having from 1 to 18 carbon atoms which is optionally substituted by fluorine, chlorine or cyano radicals and is free from ethylenically or acetylenically unsaturated bonds, and n has values from 0 to 20, where the mean number of carbon atoms of the radicals R is at most 3 and where the mixtures have evaporated, measured in accordance with DIN 53249, to an extent of from 80 to 95% by weight after 30 minutes, to an extent of from 90 to 99% by weight after 60 minutes and to an extent of from 95 to 100% by weight after 120 minutes.

The mixtures of linear organosiloxanes are added to cosmetic formulations.

20 Claims, No Drawings

MIXTURES OF VOLATILE LINEAR SILOXANES

TECHNICAL FIELD

The invention relates to mixtures of linear organosiloxanes, to processes for their preparation, and to a process for the preparation of cosmetic formulations.

BACKGROUND ART

Volatile siloxane compounds have a broad spectrum of use in a large number of areas, including in cosmetics as volatile carrier substances. Because of their low heat of evaporation, volatile siloxane compounds usually evaporate without causing a feeling of cold or burning on the skin.

Because of the high vapor pressure and the low boiling point, the volatile siloxane compounds evaporate quickly and without leaving a residue. The evaporation rate must not, however, be so great that there is insufficient time to uniformly apply, distribute, rub in, or work in the formulation containing the volatile siloxane compounds on skin, hair, etc. In addition, the treated sites should not become dried out, but should remain smooth and soft.

The siloxanes used most frequently are cyclic siloxanes having from 4 to 6 siloxane groups (commonly designated $D_4$, $D_5$, $D_6$) which contain exclusively methyl groups, and in particular, mixtures thereof, since these have a favorable rate of evaporation. However, $D_4$ is currently suspected of having a reproduction-toxic effect.

U.S. Pat. Nos. 5,002,762 and 5,084,577 describe diversely substituted linear siloxanes for use in cosmetics. Siloxane mixtures with a favorable evaporation behavior are not disclosed. The linear siloxanes in U.S. Pat. No. 5,002,762 contain, as radicals, functional groups which can undergo undesired and incalculable interactions in cosmetic formulations.

SUMMARY OF THE INVENTION

The object of the present invention is to provide volatile carrier substances suitable for use in cosmetics, which do not contain cyclic siloxanes having from 4 to 6 siloxane groups, which are very inert, and which have good compatibility with a large number of other cosmetic raw materials.

DESCRIPTION OF THE PREFERRED EMBODIMENTS

The invention provides mixtures of linear organosiloxanes of the general formula 1

$$R_3SiO\text{—}(SiR_2O)_n\text{—}SiR_3 \quad (1)$$

where

R can be identical or different and is a hydrocarbon radical having from 1 to 18 carbon atoms which is optionally substituted by fluorine, chlorine or cyano radicals and is free from ethylenically or acetylenically unsaturated bonds, and n has values from 0 to 20, where the mean number of carbon atoms of the radicals R is at most 3 and where the mixtures have evaporated, measured in accordance with DIN 53249, to an extent of from 80 to 95% by weight after 30 minutes, to an extent of from 90 to 99% by weight after 60 minutes and to an extent of from 95 to 100% by weight after 120 minutes.

The invention is based on the discovery that the mixtures of linear organosiloxanes have a considerably more favorable evaporation behavior than even the cyclic siloxanes having from 4 to 6 siloxane groups.

The rates of evaporation are measured in accordance with DIN 53249 by 1. weighing a round filter paper of diameter 150 mm,
2. applying a 0.3 ml sample using a pipette, and immediately weighing the filter and
3. weighing the filter at 5 min intervals at RT (25° C.) in a draught-free place.

In each case amounts are weighed to an accuracy of 0.001 g.

Examples of radicals R are alkyl radicals such as the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, octadecyl radicals such as the n-octadecyl radical; cycloalkyl radicals such as cyclopentyl, cyclohexyl, cycloheptyl radicals and methylcyclohexyl radicals; aryl radicals such as the phenyl, naphthyl and anthryl and phenanthryl radicals; alkaryl radicals such as o-, m-, p-tolyl radicals, xylyl radicals and ethylphenyl radicals; aralkyl radicals such as the benzyl radical and the α-and the β-phenylethyl radicals.

Examples of substituted radicals R are cyanoalkyl radicals, such as the β-cyanoethyl radical, and halogenated hydrocarbon radicals, for example halogenoalkyl radicals, such as the 3,3,3-trifluoro-n-propyl radical, the 2,2,2,2',2',2'-hexafluoroisopropyl radical, the heptafluoroisopropyl radical, and halogenoaryl radicals, such as the o-, m-, and p-chlorophenyl radicals.

Preferably, the radical R is a linear alkyl radical, in particular having from 1 to 10, in particular from 1 to 6, carbon atoms. Particularly preferred radicals R are ethyl and, in particular, methyl radicals.

n preferably has values of at most 12, in particular at most 10.

The mean number of carbon atoms of the radicals R is preferably at most 2, in particular at most 1.5.

In a preferred embodiment in which R is a methyl radical, n in 0.5 to 20% by weight of the organosiloxanes has the value 0, in 20 to 65% by weight of the organosiloxanes has the value 1, in 10 to 40% by weight of the organosiloxanes has the value 2, in 0.5 to 20% by weight of the organosiloxanes has the value 3, in 0 to 10% by weight of the organosiloxanes has the value 4, in 0 to 5% by weight of the organosiloxanes has the value 5, and in 0 to 5% by weight of the organosiloxanes has the values 6 to 20.

In a particularly preferred embodiment in which R is a methyl radical, n in 6 to 12% by weight of the organosiloxanes has the value 0, in 45 to 55% by weight of the organosiloxanes has the value 1, in 22 to 30% by weight of the organosiloxanes has the value 2, in 6 to 12% by weight of the organosiloxanes has the value 3, in 1 to 5% by weight of the organosiloxanes has the value 4, in 0 to 3% by weight of the organosiloxanes has the value 5, and in 0 to 1% by weight of the organosiloxanes has the value 6 to 20.

Preferably, the mixtures have evaporated, measured in accordance with DIN 53249, to an extent of from 20 to 80% by weight, in particular an extent of from 30 to 70% by weight after 5 minutes, and to an extent of from 60 to 90% by weight, in particular to an extent of from 70 to 85% by weight after 15 minutes.

Preferably, the mixtures have evaporated, in accordance with DIN 53249, to an extent of from 85 to 94% by weight after 30 minutes, to an extent of from 94 to 97% by weight after 60 minutes and to an extent of from 97 to 99.5% by weight after 120 minutes.

The mixtures of linear organosiloxanes are preferably prepared by hydrolyzing a mixture of 1 part of trimethylchlorosilane and from 2.5 to 6 parts, preferably from 3.5 to 4.5 parts, of dimethyldichlorosilane in hydrochloric acid.

Preferably, in a second step, excess organosiloxanes of the general formula 1 in which n has the values from 0 to 2 are separated off, preferably by distillation. In the hydrolysis, the concentration of the hydrochloric acid is preferably kept constant by metering in water. The concentration of the hydrochloric acid is preferably from 15 to 25% by weight.

The mixtures of linear organosiloxanes are used in the preparation of cosmetic formulations. The mixtures of linear organosiloxanes are advantageously used in a variety of diverse cosmetic applications, for example in formulations from the field of haircare, such as hairspray, shampoo, mousse, styling gel, styling lotion, conditioner, hair dyes, hair bleaches, etc.; formulations from the field of antiperspirants and deodorants; formulations from the field of skincare, such as body lotion, hand creams, moisturizing creams, baby creams, etc.; formulations from the field of sun protection, such as suncreams, sun milk, lip protection, etc. and formulations from the field of covering cosmetics, such as lipstick, mascara, face powder, foundation, etc.

The mixtures of linear organosiloxanes aid the uniform distribution of active ingredients on skin and hair. In decorative cosmetics, despite rapid evaporation, they offer sufficient time for processing, and as a result improve the application properties, reduce tack and make the skin smoother and softer. In haircare applications, volatile siloxane compounds aid uniform distribution of high-viscosity oils, improve wet combability and act as resin plasticizers in hair-setting/styling products.

A large number of cosmetic formulations contain fragrances. As a result of their rapid evaporation behavior at the start, in particular up to 30 min, in accordance with DIN 53249, the mixtures of linear organosiloxanes cause the top note of the fragrance used to be evident particularly quickly and prominently. As a result of the reduced evaporation rate after 30 min in accordance with DIN 53249 and the particularly greatly reduced evaporation rate up to 60 min in accordance with DIN 53249, the base note of the fragrance is retained for a particularly long period.

The invention is illustrated in more detail by reference to the examples below. All parts and percentages are by weight.

The examples are carried out at a pressure of the ambient atmosphere, i.e. at about 0.1 MPa, and at room temperature, i.e. at about 21° C.

EXAMPLES

Example 1

(Preparation)

A round-bottomed flask is charged with 100 g of a 20% strength by weight HCl solution. Over the course of 60 minutes, 560 g of a molar 4:1 mixture of dimethyldichlorosilane and trimethylchlorosilane are metered in with stirring. Water is metered in in parallel so that the concentration of the aqueous hydrochloric acid remains constant. The mixture is then stirred for 60 minutes. Following phase separation, the organic phase is washed with water until neutral. The resulting crude product is freed from most of the hexamethyldisiloxane formed in the hydrolysis/condensation by distillation, providing a final product with the following composition, where n in the general formula is as follows:

20% by weight have the value 0,

43% by weight have the value 1,

24% by weight have the value 2,

8% by weight have the value 3,

3% by weight have the value 4,

1% by weight has the value 5, and

1% by weight of the organosiloxanes have the values from 6 to 10.

Example 2

(Rates of Evaporation)

The table below lists the rates of evaporation, which were determined in accordance with DIN 53249.

| Time (min) | $D_5$ | 80% by weight of $D_4$ 20% by weight of $D_5$ | $D_4$ | Water, dist. | Example 1 |
|---|---|---|---|---|---|
| 5 | 3.51 | 19.58 | 28.64 | 27.12 | 47.49 |
| 10 | 8.05 | 36.25 | 53.15 | 48.29 | 70.43 |
| 15 | 13.34 | 53.13 | 72.11 | 72.43 | 78.49 |
| 20 | 17.76 | 69.41 | 92.85 | 89.02 | 84.85 |
| 25 | 23.45 | 79.23 | 99.41 | 97.26 | 87.88 |
| 30 | 28.49 | 86.02 | 100.00 | 98.25 | 90.67 |
| 45 | 45.64 | 96.18 | | 98.06 | 93.33 |
| 60 | 61.98 | 100.00 | | 98.59 | 96.05 |
| 90 | 89.77 | | | 98.58 | 97.38 |
| 120 | 99.01 | | | 97.52 | 98.46 |
| 180 | | | | | 99.91 |

In comparison to the advantages of the mixture of Example 1, the properties of the cyclic compounds:

$D_4$ has evaporated after 30 min in accordance with DIN 53249, and also the widespread $D_4/D_5$ mixtures (about 80/20) have evaporated after about 60 min. The evaporation behavior is likewise determined by a lower rate of evaporation than for the mixture of Example 1. For comparison: $D_5$ has evaporated to an extent of 99% after 120 min; but to an extent of only about 29% after 30 min and to an extent of about 62% after 60 miin, as a result of which it is not possible to avoid a wet, oily feel on use of the formulation.

Example 3

(Cosmetic Formulations Comprising the Mixture of Example 1)

Compared with cyclic compounds ($D_4$, $D_5$ and 80/20 $D_4/D_5$ mixture) there was no important discernible difference in the processing. The optical appearance of the formulations remained unchanged.

a) Antiperspirant Stick

Solid stick with slightly soft rub-off.

| | |
|---|---|
| A | 18.00% of stearic acid |
| | 18.00% of cetyl alcohol |
| | 24.00% of aluminum chlorohydrate |
| B | 40.00% of a mixture of Example 1 |
| | according to requirement, fragrances, dyes | mix A and heat to 75–80° C., mix B into A.

Comparison: Mixture of Example 1 is replaced by the same amount of $D_5$.

Remark: In the case of formulation a) a drier feel on the skin after less time.

b) Deodorant Pump Spray

Colorless, clear, low-viscosity 30.00% of ethanol
69.00% of a mixture of Example 1
1.00% of fragrance All components are thoroughly mixed.

Comparison: Mixture of Example 1 is replaced by the same amount of $D_5$.

Remark: Formulation b) absorbs more quickly than in comparison; pleasant dry feel on the skin after less time.

c) Bath Oil

Colorless, slightly cloudy, low-viscosity.

25.00% of a mixture as in Example 1
70.00% of avocado oil
5.00% of PPG-15 stearyl ether according to requirement, preservatives, dyes, fragrances mix all components.

Comparison: Mixture of Example 1 is replaced by the same amount of an 80/20 $D_4/D_5$ mixture.

Remark: Formulation c) exhibits better compatibility than comparison; absorbs more easily.

d) Sunscreen Oil

Colorless, clear, low-viscosity.

| | |
|---|---|
| A | 10.00% of a mixture as in Example 1 |
| | 10.00% of isopropyl myristate |
| | 77.00% of paraffin oil |
| B | 3.00% of octyl methoxycinnamate | according to requirement, preservatives, dyes, fragrances mix A, add B, mix.

Comparison: Mixture of Example 1 is replaced by the same amount of an 80/20 $D_4/D_5$ mixture.

Remark: Formulation d) absorbs more quickly than comparison; earlier pleasant dry feel on the skin e) Sunscreen Oil Colorless, clear, low-viscosity.

| | |
|---|---|
| A | 40.00% of a mixture as in Example 1 |
| | 10.00% of isopropyl myristate |
| | 47.00% of oleyl oleate |
| B | 3.00% of octyl methoxycinnamate | according to requirement, preservatives, fragrances, dyes mix A, add B, mix.

Comparison: Mixture of Example 1 is replaced by the same amount of 30% of $D_5$ and 10% of hexamethyldisiloxane.

Remark: Formulation e) absorbs more quickly than comparison; earlier pleasant dry feel on the skin.

f) Face Powder

Homogeneous powder.

| | | |
|---|---|---|
| A | 74.00% | talc |
| | 6.00% | of magnesium stearate |
| | 3.00% | of acrylates/$C_{10-30}$-alkyl acrylate crosspolymer |
| B | 12.00% | of a mixture as in Example 1 |
| | 2.00% | of hydrolyzed animal protein (INCI) |
| C | 0.20% | of methylparaben |
| | 1.90% | of talc |
| | 0.70% | of pigments | according to requirement, fragrances, dyes mix A well, mix in B in portions, add C, mix in D homogeneously.

Comparison: Mixture of Example 1 is replaced by the same amount of $D_5$.

Remark: Formulation f) can be distributed more finely on the skin than comparison; no formation of lumps/layers g) Care Cream White solid cream, easy to disperse, velvety feel on the skin.

| | |
|---|---|
| A | 3.85% of polysorbate-60 |
| | 7.69% of cetearyl alcohol |
| | 19.23% of petrolatum (INCI) |
| B | 38.46% of water |
| | 7.69% of glycerol |
| C | 23.08% of a mixture as in Example 1 | according to requirement, preservatives, fragrances heat each of A and B to 70° C. Mix B into A.

h) Deodorant stick Cream-colored stick with gentle rub-off

| | |
|---|---|
| 1.00% | of zinc ricinoleate, triethanolamine, dipropylene glycol, lactic acid |
| 8.50% | of sodium stearate |
| 5.50% | of glycerol |
| 4.00% | of a mixture as in Example 1 |
| 70.40% | of propylene glycol |
| 10.00% | of ethanol |
| 0.60% | of hydroxyethylcellulose | according to requirement, fragrances, dyes mix and melt all of the components. Draw off the homogeneous solution while hot.

Comparison: Mixture of Example 1 is replaced by the same amount of $D_5$.

Remark: In the case of formulation h) a drier feel to the skin is achieved earlier.

i) Cover Cream
Soft homogeneous cream.

| A | 5.50% of candelille wax |
| | 6.70% of Stearoxy Dimethicone (INCI) |
| | 3.00% of stearic acid |
| B | 44.80% of water |
| | 3.40% of propylene glycol |
| | 1.30% of triethanolamine |
| C | 14.00% of titanium dioxide |
| D | 18.30% of a mixture of Example 1 | according to requirement, preservatives, perfume, dyes

Heat each of A and B to 70° C. Mix B into A. Incorporate C homogeneously. Allow to cool slightly, stir in D at about 30° C.

Comparison: Mixture of Example 1 is replaced by the same amount of $D_5$.

Remark: Formulation i) can be distributed more easily and is more water-resistant than comparison.

k) Deodorant Stick
Solid, slightly yellowish stick with gentle rub-off

| 50.00% | of wool wax acid |
| 36.00% | of Stearoxy Dimethicone (INCI) |
| 5.00% | of isopropyl myristate |
| 4.00% | of dimethicone, viscosity 350 mm²/sec |
| 5.00% | of a mixture of Example 1 | according to requirement, fragrances, dyes
melt all of the components together.

Comparison: Mixture of Example 1 is replaced by the same amount of $D_5$.

Remark: Formulation k) exhibits slightly less and gentler rub-off than comparison sample.

l) Bath Oil
Yellowish, clear, low-viscosity

| A | 1.00% | of Stearoxy Dimethicone (INCI) |
| | 69.00% | of jojoba oil |
| | 25.00% | of a mixture as in Example 1 |
| | 5.00% | of polypropylene glycol-15 stearyl ether | according to requirement, preservatives, dyes, fragrances
heat A to 50° C., mix B into A.

Comparison: Mixture of Example 1 is replaced by the same amount of $D_5$.

Remark: formulation l) exhibits better distribution in the bath water.

m) Sunscreen Oil
Yellowish, clear, low-viscosity.

| 60.00% | of a mixture as in Example 1 |
| 10.00% | of dimethiconol, dimethicone viscosity > 10 mm²/s |
| 10.00% | of diisopropyl adipate |
| 7.00% | of octyl methoxycinnamate |
| 3.00% | of benzophenone-3 |
| 10.00% | of $C_{12-15}$-alkyl benzoate | according to requirement, preservatives, fragrances, dyes
mix all of the components well and filter.

Comparison: Mixture of Example 1 is replaced by the same amount of $D_5$.

Remark: Formulation m) absorbs more quickly than comparison, pleasant dry feel on the skin after less time.

What is claimed is:

1. A mixture of linear organosiloxanes of the general formula 1

$$R_3SiO\text{---}(SiR_2O)_n\text{---}SiR_3 \quad (1),$$

where

R can be identical or different and is a hydrocarbon radical having from 1 to 18 carbon atoms which is optionally substituted by fluorine, chlorine or cyano radicals and is free from ethylenically or acetylenically unsaturated bonds, and n has values from 0 to 20, where the mean number of carbon atoms of the radicals R is at most 3 and where the mixture has evaporated, measured in accordance with DIN 53249, to an extent of from 80 to 95% by weight after 30 minutes, to an extent of from 90 to 99% by weight after 60 minutes and to an extent of from 95 to 100% by weight after 120 minutes.

2. A process for the preparation of the mixture of claim 1, in which a mixture of 1 part of trimethylchlorosilane and from 2.5 to 6 parts of dimethyldichlorosilane is hydrolyzed in hydrochloric acid, wherein R is a methyl radical, and the distribution of oligomers is such that for n, 0.5 to 20% by weight of the organosiloxanes has the value 0, in 20 to 65% by weight of the organosiloxanes has the value 1, in 10 to 40% by weight of the organosiloxanes has the value 2, in 0.5 to 20% by weight of the organosiloxanes has the value 3, in 0 to 10% by weight of the organosiloxanes has the value 4, in 0 to 5% by weight of the organosiloxanes has the value 5, and in 0 to 5% by weight of the organosiloxanes has the values 6 to 20, and at least one cosmetically acceptable ingredient other than said mixture of claim 1.

3. A cosmetic formulation which comprises the mixture of claim 1.

4. A cosmetic formulation which comprises the mixture of claim 1, wherein R is a methyl radical, and the distribution of oligomers is such that for n, 0.5 to 20% by weight of the organosiloxanes has the value 0, in 20 to 65% by weight of the organosiloxanes has the value 1, in 10 to 40% by weight of the organosiloxanes has the value 2, in 0.5 to 20% by weight of the organosiloxanes has the value 3, in 0 to 10% by weight of the organosiloxanes has the value 4, in 0 to 5% by weight of the organosiloxanes has the value 5, and in 0 to 5% by weight of the organosiloxanes has the values 6 to 20, and at least one cosmetically acceptable ingredient other than said mixture of claim 1, and which contains at least one cosmetically acceptable ingredient other than said mixture.

5. A cosmetic formulation which comprises the mixture of claim 1, wherein R is a linear alkyl radical having from 1 to 10 carbon atoms.

6. The cosmetic formulation of claim 5, wherein n has values of at most 12.

7. The cosmetic formulation of claim 3, wherein the mean number of carbon atoms of the radicals R is at most 2.

8. The cosmetic formulation of claim 3, wherein the mixture has evaporated, measured in accordance with DIN 53249, to an extent of from 20 to 80% by weight after 5 minutes, and to an extent of from 60 to 90% by weight after 15 minutes.

9. The cosmetic formulation of claim 3, wherein R is a methyl radical, and the distribution of oligomers is such that for n, 0.5 to 20% by weight of the organosiloxanes has the value 0, in 20 to 65% by weight of the organosiloxanes has the value 1, in 10 to 40% by weight of the organosiloxanes has the value 2, in 0.5 to 20% by weight of the organosiloxanes has the value 3, in 0 to 10% by weight of the organosiloxanes has the value 4, in 0 to 5% by weight of the organosiloxanes has the value 5, and in 0 to 5% by weight of the organosiloxanes has the values 6 to 20.

10. The cosmetic formulation of claim 3, wherein R is a methyl radical, and the distribution of oligomers is such that for n, 6 to 12% by weight of the organosiloxanes has the value 0, in 45 to 55% by weight of the organosiloxanes has the value 1, in 22 to 30% by weight of the organosiloxanes has the value 2, in 6 to 12% by weight of the organosiloxanes has the value 3, in 1 to 5% by weight of the organosiloxanes has the value 4, in 0 to 3% by weight of the organosiloxanes has the value 5, and in 0 to 1% by weight of the organosiloxanes has the value 6 to 20.

11. The cosmetic formulation of claim 3 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

12. The cosmetic formulation of claim 4 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

13. The cosmetic formulation of claim 5 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

14. The cosmetic formulation of claim 6 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

15. The cosmetic formulation of claim 7 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

16. The cosmetic formulation of claim 8 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

17. The cosmetic formulation of claim 9 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

18. The cosmetic formulation of claim 10 further comprising one or more cosmetically accepted ingredients selected from the group consisting of antiperspirants, pigments, flavorants, odorants, ultraviolet absorbers, vegetable oils, mineral oils, aliphatic glycols, glycerine, fatty alcohols, and alkanol fatty acid esters.

19. The cosmetic formulation of claim 3 which is a deodorant.

20. The cosmetic formulation of claim 3 which is a care cream.

* * * * *